(12) United States Patent
Hussain et al.

(10) Patent No.: US 9,176,056 B2
(45) Date of Patent: Nov. 3, 2015

(54) MEASUREMENT APPARATUS AND METHOD

(75) Inventors: Shahid Hussain, Reading (GB); Greg Peter Wade Fixter, Hook (GB); Stefan Szwarnowski, Malvern (GB)

(73) Assignee: QINETIQ LIMITED, Hampshire (GB)

( * ) Notice: Subject to any disclaimer, the term of this patent is extended or adjusted under 35 U.S.C. 154(b) by 584 days.

(21) Appl. No.: 13/520,750

(22) PCT Filed: Jan. 24, 2011
(Under 37 CFR 1.47)

(86) PCT No.: PCT/GB2011/000084
§ 371 (c)(1),
(2), (4) Date: Sep. 25, 2012

(87) PCT Pub. No.: WO2011/089399
PCT Pub. Date: Jul. 28, 2011

(65) Prior Publication Data
US 2013/0077098 A1 Mar. 28, 2013

(30) Foreign Application Priority Data

Jan. 25, 2010 (GB) .................................. 1001131.0

(51) Int. Cl.
*G01N 21/55* (2014.01)
*G01N 22/00* (2006.01)
*G01S 7/41* (2006.01)

(52) U.S. Cl.
CPC ............... *G01N 21/55* (2013.01); *G01N 22/00* (2013.01); *G01S 7/411* (2013.01)

(58) Field of Classification Search
CPC .. G01B 11/06; G01B 11/026; G01B 11/0625; G01B 11/14; G01B 11/245; G01N 22/00
See application file for complete search history.

(56) References Cited

U.S. PATENT DOCUMENTS

| | | | | |
|---|---|---|---|---|
| 5,422,703 A | * | 6/1995 | Horie et al. | 356/445 |
| 6,373,573 B1 | * | 4/2002 | Jung et al. | 356/419 |
| 2007/0285643 A1 | * | 12/2007 | Wedowski et al. | 355/67 |

FOREIGN PATENT DOCUMENTS

| | | |
|---|---|---|
| CN | 101101267 A | 1/2008 |
| DE | 43 42 288 A1 | 6/1995 |
| EP | 1 211 504 A2 | 6/2002 |
| GB | 2 242 532 A | 10/1991 |
| GB | 2458998 A | 10/2009 |
| JP | A-2004-156987 | 6/2004 |

(Continued)

OTHER PUBLICATIONS

Search Report issued in British Application No. 1001131.0 dated Mar. 25, 2010.
Sakran et al., "Absorbing Frequency-Selective-Surface for the mm-Wave Range," *IEEE Transactions on Antennas and Propagation*, vol. 56, No. 8, Aug. 2008, pp. 2649-2655.

(Continued)

*Primary Examiner* — Tung X Nguyen
(74) *Attorney, Agent, or Firm* — Oliff PLC

(57) ABSTRACT

A method of measuring the reflectivity of a region of an article to electromagnetic radiation, in particular for the characterisation of the radio-frequency (RF) properties of wind turbine blades. The article is arranged in the near-field of a transceiver antenna, which performs both illumination and measurement of reflected radiation from the region of the article undergoing measurement. The method is beneficial in that it can be used with an antenna in close proximity (or in contact) to the article to be measured, for example for use in on site measurement of specific regions of a turbine blade.

23 Claims, 3 Drawing Sheets

(56) References Cited

FOREIGN PATENT DOCUMENTS

| WO | WO 00/03253 A1 | 1/2000 |
| WO | WO 01/42737 A1 | 6/2001 |
| WO | WO 2005/045450 A1 | 5/2005 |
| WO | WO 2010/109174 A1 | 9/2010 |

OTHER PUBLICATIONS

International Search Report issued in International Patent Application No. PCT/GB2011/000084 dated May 16, 2011.
Written Opinion issued in International Patent Application No. PCT/GB2011/000084 dated May 16, 2011.

\* cited by examiner

MEASUREMENT APPARATUS AND METHOD

BACKGROUND

The present invention relates to a method of measuring the reflectivity or absorbency of an item to electromagnetic radiation and to a reflectometer for performing said method. Without limitation, the invention also relates to a method of determining the dielectric properties, for example relative permittivity, of said item and to a measurement apparatus for performing said method. Such a method and apparatus are suitable for non-destructive, quality assurance assessments of items during manufacture. Without limitation, the present method and apparatus find application in the characterisation of the radio-frequency (RF) properties of wind turbine blades.

Radar absorbing materials (RAMs) are employed in composite aerofoil structures such as aircraft wings and wind turbine blades in order to reduce the radar cross-section (RCS) of said structures. This is particularly important for new wind farms in order to reduce undesirable effects of the wind turbine blades on air-traffic control (ATC) radar and air-defence radar (ADR).

SUMMARY

A conventional technique for measuring the RF characteristics of a large composite structure such as a wind turbine blade is to measure the overall radar cross-section thereof using a conventional radar apparatus. This technique can provide a useful indication of the RF reflectivity of the structure as a whole. However, the technique is restricted to in-situ measurements of composite structures in the external environment; the technique cannot be used for quality assurance purposes within a factory because of interference caused by unwanted radar reflections from the surrounding environment.

An alternative technique for measuring the RF characteristics of composite materials is to measure the RF transmission or reflectivity of a sample of the material within an RF waveguide. This technique enables characterisation of small samples of composite material, however the system cannot be used for quality assurance purposes for completed composite structures.

It is an object of the invention to provide a measurement method and apparatus which mitigates at least one disadvantage of conventional RF measurement methods and apparatuses.

According to a first aspect of the present invention, there is now proposed a method of measuring the reflectivity of a region of an article to electromagnetic radiation comprising the steps of:
a) arranging the article in the near-field of a transceiver antenna,
b) illuminating the region of the article with electromagnetic radiation transmitted from the antenna over a desired frequency range,
c) receiving electromagnetic radiation reflected from the region of the article in the near-field of the antenna using said antenna,
d) measuring the reflected radiation and determining therefrom the reflectivity of said article in said region.

The present method is advantageous in that it only requires one transceiver antenna (and therefore a one port S11 measurement) to perform both the illuminating and the measuring steps and hence to carry out a reflectivity measurement, instead of the conventional two-antenna technique.

The present method is also beneficial in that it can be used with an antenna in close proximity (or in contact) to the article to be measured. This reduces the size of the sample required for an effective measurement. This is particularly useful for articles where many regions are too small for conventional measurements, e.g. articles such as aerofoil structures and in particular wind turbine blades.

Because the method only uses one transceiver antenna in close proximity (and potentially shorter cables), this technique is versatile and simple to use, which is crucial for on-site measurements.

The near-field of the transceiver antenna (sometimes known as the near zone) would be understood to be that region in close proximity to said transceiver antenna, and can be considered as the region in which angular field distribution is dependent upon distance from the antenna.

Roughly speaking, the near field is the region within a radius r of the antenna wherein r is of the order of, or less than the wavelength $\lambda$ of the electromagnetic radiation transmitted from the antenna.

The near-field of the transceiver antenna may also be considered in terms of the propagation properties of the antenna. For example, in a system comprising transmitter and receiver antennas, if the distance separating said antennas is less than $2D^2/\lambda$, where D is the largest dimension of the antenna aperture, then measurements are generally considered to be near-field measurements (Fresnel zone).

In addition, or as an alternative to reference to the near-field, the arrangement of the article relative to the transceiver in aspects of the invention may be described in terms of numerical ranges: advantageously, the stand off distance, or the arrangement of the article or measurement region from the antenna is in the range 0.2-1.2 or 0.6-1.2 meters, or in the range 50-500 mm, or 100-300 mm. In particular 0.12 meters from the antenna and 0.3 meters from the antenna have been found to be desirable stand off ranges. The skilled person would understand that said range is typically measured from the emitting/receiving aperture of the antenna, e.g. from the position at which free-space propagation of the electromagnetic radiation occurs.

In a preferred embodiment, the measuring step comprises measuring at least one of the magnitude and phase of the electromagnetic radiation reflected from said region of said article.

Conveniently, the measuring step comprises at least one of an S11 and an S22 reflectivity measurement.

In another embodiment, the method may comprise determining the reflectivity using only reflected electromagnetic radiation received at the antenna within a predefined temporal window following the transmission of said electromagnetic radiation.

The step of using time domain gating of the measured reflected electromagnetic radiation is beneficial in that it reduces unwanted reflections between the antenna and article to be measured. A time gate of 2 ns is used in preferred embodiments.

The method is particularly advantageous in that it overcomes the problems of multiple reflection between the antenna and article to be measured, ie source & test port mismatch, which would otherwise inhibit the use of one-antenna measurement techniques.

Advantageously, the illuminating step may comprise illuminating the region with electromagnetic radiation having one of single and dual polarisation in a beam having a Gaussian intensity profile, and wherein the measuring step comprises measuring the reflected electromagnetic radiation at the or each polarisation state.

In a preferred embodiment, the electromagnetic radiation has a frequency in the range 1-20 GHz, particularly in the range 1-5 GHz, in particular about 3 GHz. It is desirable for a frequency sweep to be performed, covering a defined frequency range about a central frequency, and a sweep across the range 2-5 GHz has been found to provide useful results.

The method may also comprise the step of determining at least one of the electromagnetic absorbency, a dielectric property and the relative permittivity of said article in said region from the determined electromagnetic reflectivity.

Preferably, the method comprises the step of measuring the reflectivity of a plurality of regions of said article to electromagnetic radiation.

In one embodiment, the method further includes a calibration step comprising:
e) measuring the electromagnetic reflectivity of a substantially reflective material and calibrating the determining step to provide a determined reflectivity of $0(\pm1)$dB, and
f) measuring the electromagnetic reflectivity of a substantially absorptive material and calibrating the determining step to provide a determined reflectivity loss of >25 dB.

This two-stage calibration step provides the advantage that tracking and directivity errors may be reduced or eliminated. The present calibration method is beneficial in that only two calibration measurements are required, i.e. a 'short' measurement of a substantially reflective calibration sample and a 'load' measurement of a substantially absorbing calibration sample. This obviates an intermediate measurement which is traditionally required with a conventional three-stage calibration process, such as a load measurement or an offset short.

Advantageously, the method comprises the step of aligning the antenna along a direction substantially orthogonal to a surface of the region to be measured and at a predetermined distance from said surface.

The alignment step may include providing at least one substantially rigid spacing member in mechanical communication with the article and the antenna so as to align the antenna.

In one embodiment, the spacing member comprises a plurality of legs depending from the antenna.

In another embodiment, the spacing member comprises an optical element comprising a polymer foam disposed between the antenna and the article and wherein the illuminating and measuring steps are performed through said optical element.

The polymer foam optical element enables a free-space, contacting measurement technique to be employed which provides benefits in terms of maintaining a constant distance and angle of illumination between the antenna and the surface of the article to be measured. The measurements are free-space measurements in that the polymer foam optical element does not exhibit waveguide properties.

Advantageously, the polymer foam has a permittivity substantially the same as air.

Preferably, the polymer foam comprises at least one of a synthetic polymer foam, a closed cell polymer foam, a microcellular polymer foam, a polythene foam and expanded polystyrene.

According to a second aspect of the present invention, there is now proposed a method of measuring the electromagnetic reflectivity of an aerofoil structure, in particular a wind-turbine blade, using a method according to the first aspect of the invention.

According to a third aspect of the present invention, there is now provided a reflectometer comprising a transceiver antenna having a spacing member depending there-from, the spacer member defining a measurement region within the near-field of the antenna within which to admit articles to be measured.

The reflectometer provides an apparatus for conveniently measuring the electromagnetic reflectivity of articles placed within the measurement region.

The present reflectometer is advantageous in that it only requires one transceiver antenna (and therefore a one port S11 measurement) to perform both the illuminating and the measuring steps and hence to carry out a reflectivity measurement, instead of the conventional two-antenna technique.

The present reflectometer is also beneficial in that it is used with an antenna in close proximity (or in contact) to the article to be measured. This reduces the size of the sample required for an effective measurement. This is particularly useful for articles where many regions are too small for conventional measurements, e.g. articles such as aerofoil structures and in particular wind turbine blades.

Because the reflectometer only uses one transceiver antenna in close proximity (and potentially shorter cables), this technique is versatile and simple to use, which is crucial for on-site measurements.

In one embodiment, the spacing member comprises a plurality of legs depending from the antenna.

In another embodiment, the spacing member comprises an optical element arranged in optical and mechanical communication with the antenna, the optical element having a substantially planar surface within the measurement region, said planar surface being arranged substantially orthogonal to a transceiving axis of the antenna.

The transceiving axis is the main axis of the antenna along which electromagnetic radiation is transmitted and received.

Preferably, the optical element comprises a polymer foam having a permittivity substantially the same as air.

Conveniently, the polymer foam comprises at least one of a synthetic polymer foam, a closed cell polymer foam, a microcellular polymer foam, a polythene foam, and expanded polystyrene.

Preferably, the antenna comprises a microwave horn antenna.

In a preferred embodiment, the reflectometer is adapted in use to emit a beam of microwave radiation having one of single and dual polarisation, and a substantially Gaussian intensity profile.

In one embodiment, the reflectometer includes a source of electromagnetic radiation having a frequency in the range 0.5-20 GHz, particularly in the range 1-5 GHz, in particular about 3 GHz. Preferably, the reflectometer comprises a receiver sensitive to said electromagnetic radiation.

Where the reflectometer comprises a source and a receiver, said source and receiver are configured in use to perform one of an S11 and an S22 reflectivity measurement.

Advantageously, the reflectometer comprises a processor arranged in use to determine the reflectivity of an article disposed within the measurement region. To this end, the reflectometer may comprise a Vector Network Analyser (VNA).

A further aspect of the invention proposes the use of an apparatus according to the third aspect of the invention to measure the electromagnetic reflectivity of an aerofoil structure, in particular a wind-turbine blade.

The invention extends to methods, apparatus and/or use substantially as herein described with reference to the accompanying drawings.

Any feature in one aspect of the invention may be applied to other aspects of the invention, in any appropriate combination. In particular, method aspects may be applied to apparatus aspects, and vice versa.

BRIEF DESCRIPTION OF THE DRAWINGS

Preferred features of the present invention will now be described, purely by way of example, with reference to the accompanying drawings, in which.

DETAILED DESCRIPTION OF THE EMBODIMENTS

Figure 1:
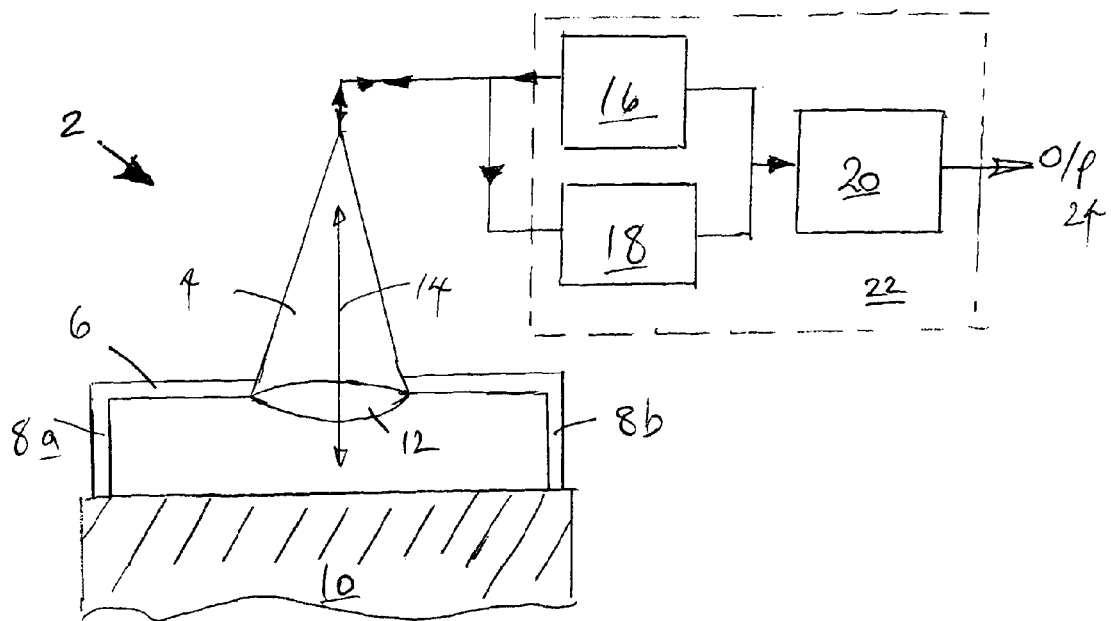
FIG. 1 shows a schematic cross-sectional view of a reflectometer according to one embodiment of the present invention incorporating a stand mounted horn antenna.

Referring now to the drawings wherein like reference numerals identify corresponding or similar elements throughout the several views, FIG. 1 shows a reflectometer 2 comprising an antenna horn 4 mounted on a spacing member comprising a stand 6, the stand having legs 8a, 8b depending there-from. Most of Applicant's experimental work has been carried out using a DP240 dual-polar horn antenna manufactured by Flann Microwave, but other antennas may be applicable. The stand 6 and legs 8a, 8b are arranged so as to define a measurement region within which an article to be measured 10 is admitted. The stand 6 and legs are substantially rigid to ensure that the antenna horn 4 remains at a predetermined, fixed distance from the article to be measured 10.

The antenna horn 4 is a combined transmitter and receiver antenna (transceiver antenna) adapted to transmit and receive electromagnetic radiation along a transceiving axis 14. The horn antenna 4 optionally comprises a dielectric lens 12 through which said electromagnetic radiation is transmitted and received. The dielectric lens 12 imparts a Gaussian intensity profile to the electromagnetic radiation. The antenna horn 4 is mounted in the frame 6 such that the transceiving axis thereof is substantially orthogonal to the surface of the article to be measured 10 when legs 8a, 8b are in contact said surface.

The antenna horn 4 is connected to a source 16 of electromagnetic radiation and a receiver 18 adapted to receive and measure electromagnetic radiation reflected from the article to be measured 10. A measurement output from the receiver 18 is input to a processor 20 which is configured to determine the reflectivity of the article to be measured 10. Optionally, an output from the source 16 is also input to the processor 20. The processor 20 has an output 24 for providing a determination of the reflectivity of the article 10. Optionally, the source 16, the receiver 18 and the processor 20 are combined within a Vector Network Analyser (VNA) 22, for example an HP8722C VNA or an Anritsu MS2028B VNA.

Figure 2:
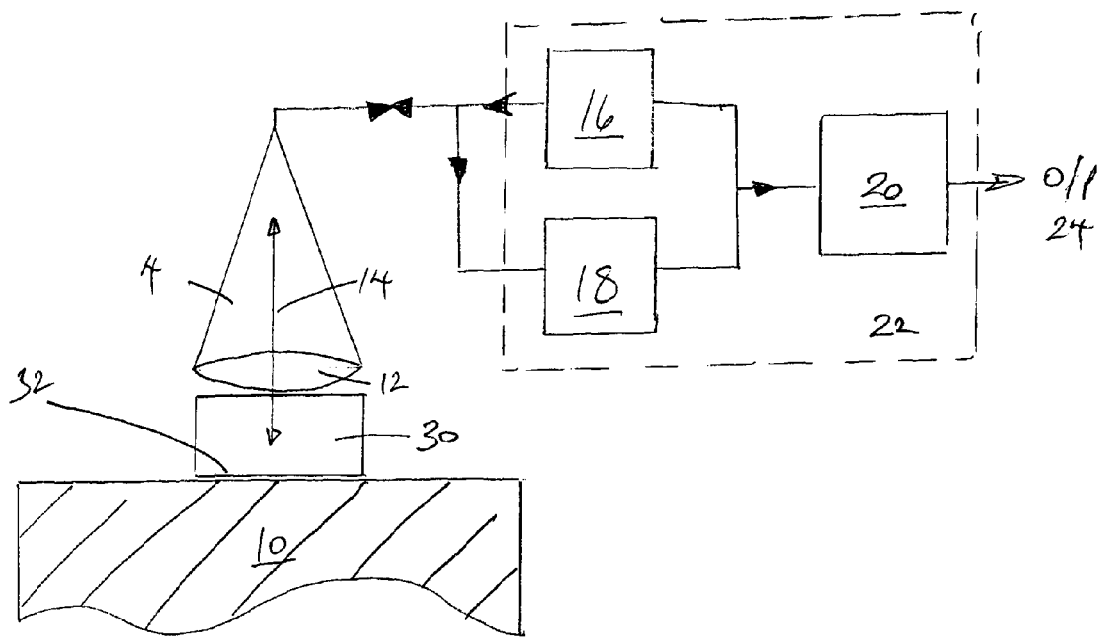
FIG. 2 shows a schematic cross-sectional view of a reflectometer according to a second embodiment of the present invention incorporating a polymer foam spacing member disposed between the horn antenna and the article to be measured.

An alternative reflectometer is illustrated in FIG. 2 wherein like reference numerals identify corresponding or similar elements to those of the first embodiment shown in FIG. 1.

In common with the embodiment of FIG. 1, the reflectometer of FIG. 2 comprises a combined transmitter and receiver antenna (transceiver antenna) adapted to transmit and receive electromagnetic radiation along a transceiving axis 14. The horn antenna 4 may comprise a dielectric lens 12 through which to transmit and receive said electromagnetic radiation.

However, in FIG. 2, the antenna horn 4 is arranged in contact with a spacing member comprising a polymer foam optical element 30. The polymer foam optical element 30 has a substantially planar surface 32 facing away from the antenna 4, which surface 32 defines a measurement region within which to admit the article 10 to be measured. The polymer foam is substantially rigid to ensure that the antenna horn 4 remains at a predetermined, fixed distance from the article to be measured 10 throughout the measurement process.

The antenna horn 4 is arranged such that the transceiving axis 14 thereof is substantially orthogonal to the planar surface 32 of the polymer foam optical element. In use, the substantially planar surface 32 is arranged in contact with a surface of the article to be measured 10. This arrangement ensures that transceiving axis 14 of the antenna horn 4 remains substantially orthogonal to the surface of the article to be measured 10 throughout the measurement process. Where the surface of the article to be measured 10 is curved, this arrangement ensures that transceiving axis 14 of the antenna horn 4 remains substantially orthogonal to a plane arranged at a tangent to said curved surface.

The optical element 30 comprises a polymer foam material which has a permittivity substantially the same as that of air. For example, the relative permittivity of the polymer foam optical element was measured as 1.03, which is so low as not to interfere with the electromagnetic radiation passing therethrough. Polymer foam materials having a relative permittivity of less than or equal to 1.1, 1.2, or possibly even 1.5 would appear suitable for use in the present reflectometer.

The reflectometer of FIG. 2 enables free-space electromagnetic reflectivity measurements to be made of the article to be measured 10, while the mechanical communication between the antenna horn 4, the polymer foam optical element 30 and the article to the measured 10 ensures that the predetermined distance between the antenna horn 4 and the article to be measured 10 remains substantially constant throughout the measurement process. This configuration also ensures that the angle of incidence of the electromagnetic radiation with respect to the surface of the article to be measured 10 remains substantially constant throughout the measurement process.

As before, the antenna horn 4 is connected to a source 16 of electromagnetic radiation and a receiver 18 adapted to receive and measure electromagnetic radiation reflected from the article to be measured 10. A measurement output from the receiver 18 is input to a processor 20 which is configured to determine the reflectivity of the article to be measured 10. Optionally, an output from the source 16 is also input to the processor 20. The processor 20 has an output 24 for providing a determination of the reflectivity of the article 10. Optionally, the source 16, the receiver 18 and the processor 20 are combined within a Vector Network Analyser (VNA) 22, for example an HP8722C VNA or an Anritsu MS2028B VNA.

A method of measuring the reflectivity of a region of an article to electromagnetic radiation according to one embodiment of the present invention is now described. The measurement method utilises the reflectometer described herein before to take S11 or S22 reflectivity measurements of the article. The beam width allows for a minimum sample size of 300×300 mm to be measured.

The present measurement method advantageously provides two standards to be measured as part of a calibration procedure. The first is known as the 'short circuit' and provides a measure of 'perfect' reflectivity. The second is the 'load' and provides a measure of 'perfect' absorption. Any reflectivity measurements made on the article under test are calculated relative to the two standards. Reflectivity calculations and data smoothing (time domain gating) are either be made on the receiver 18 and processor 20 (optionally a Vector Network Analyser where applicable) or off-line, for example on a MathCad program.

The reflectometer 2 is calibrated as follows. Firstly, the 'short circuit' performance of the reflectometer 2 is determined by placing a metal plate in the measurement region and an S11 reflectivity measurement is made. The reflectometer is adjusted to ensure that an S11 reflectivity of 0(±1)dB is produced. Secondly, the 'load' performance of the reflectometer 2 is determined by placing a pyramidal absorber in the sample position and an S11 reflectivity measurement is made. The reflectometer is adjusted to ensure that an S11 reflectivity loss >25 dB is produced. The order in which the calibration measurements are made is not important.

Measurements of the electromagnetic reflectivity of an article are conducted as follows. Antenna horn 4 is arranged in contact with the polymer foam optical element 30 which is in turn arranged in contact with the surface of the article to be measured 10. The thickness of the polymer foam optical element 30 (i.e. the distance between the antenna horn 4 and the surface of the article to be measured 10) was arranged to be 0.12 meters in Applicant's experimental evaluations.

The article to be measured 10 is then illuminated with electromagnetic radiation over a desired frequency range (generated by the source 16) transmitted from the horn antenna 4 through the polymer foam optical element 30. Electromagnetic radiation reflected from the article to be measured 10 is received by the horn antenna 4 and the receiver 18. Said reflected electromagnetic radiation is measured and a determination made there-from of the reflectivity of said article.

The measuring step comprises measuring at least one of the magnitude and phase of the electromagnetic radiation reflected from the article 10. An S11 reflectivity measurement is made where the horn antenna 4 comprises a single polarisation antenna. Optionally, an S22 reflectivity measurement is made where the horn antenna 4 comprises a dual polarisation antenna.

Measurement of the electromagnetic radiation reflected from the article to be measured 10 may be controlled using a time domain gate to reduce interference caused by unwanted reflections in the free-space region between the antenna horn 4 and the surface of the article to be measured 10. In this case, the reflectivity is determined using only reflected electromagnetic radiation received at the antenna within a predefined temporal window following the transmission of said electromagnetic radiation. A temporal window having a duration of 2 ns was found to be generally sufficient during Applicant's experiments, however this can change for different system configurations.

A method of measuring the reflectivity of article using the apparatus of FIG. 2 including an HP8722C VNA is as follows.

The horn antenna 4 is connected to port 1 of the HP 8722C VNA for a single channel (Channel 1) S11 reflectivity measurement. This is then calibrated on Channel 1 of the VNA for S11 measurements, as described with relation to the calibration method above. Optionally, for a dual polarisation (dual channel) measurement, such that the response of the article 10 in both polarisations is measured simultaneously using an S11 and S22 measurement, a second cable is connected from the alternative connection on the horn antenna 4, to port 2 of the VNA. This is then calibrated on Channel 2 of the VNA for S22 measurements, as described with relation to the calibration method above.

After measuring, gating and saving the channel 1 (S11 reflectivity) data, the VNA is switched to channel 2 (S22 reflectivity) and the measurement procedure repeated, ensuring the measurement is separately triggered under each channel.

Figure 3:
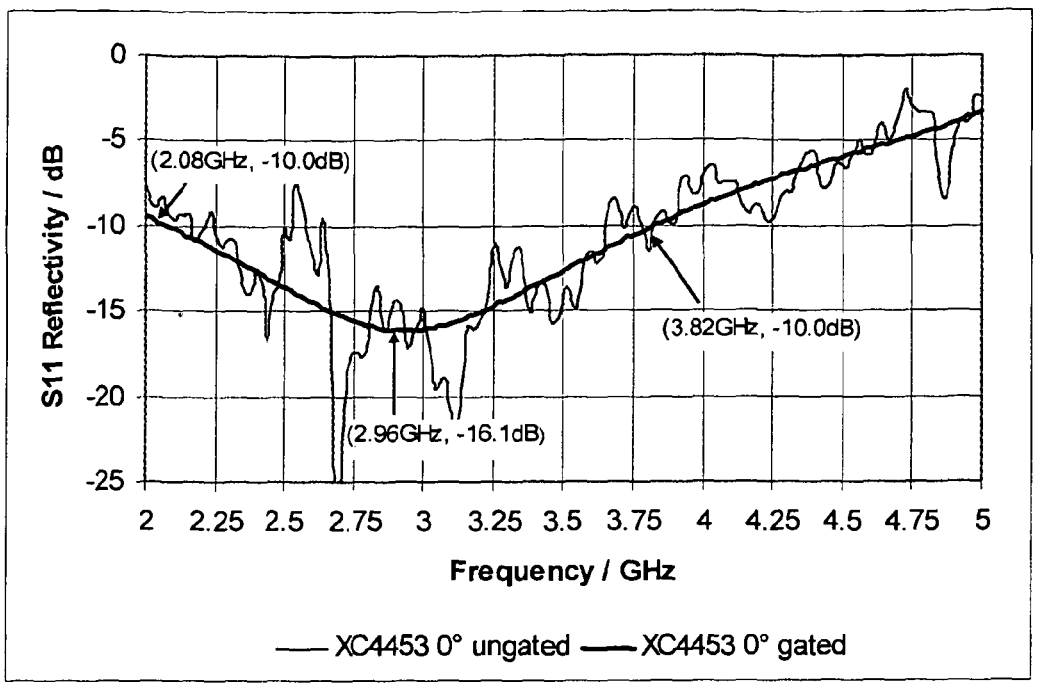
FIG. 3 shows a graph of electromagnetic reflectivity versus frequency of electromagnetic radiation measured using an HP8722C Vector Network Analyser (VNA) for a sample article reference XC4453 at 0° sample orientation.
Figure 4:
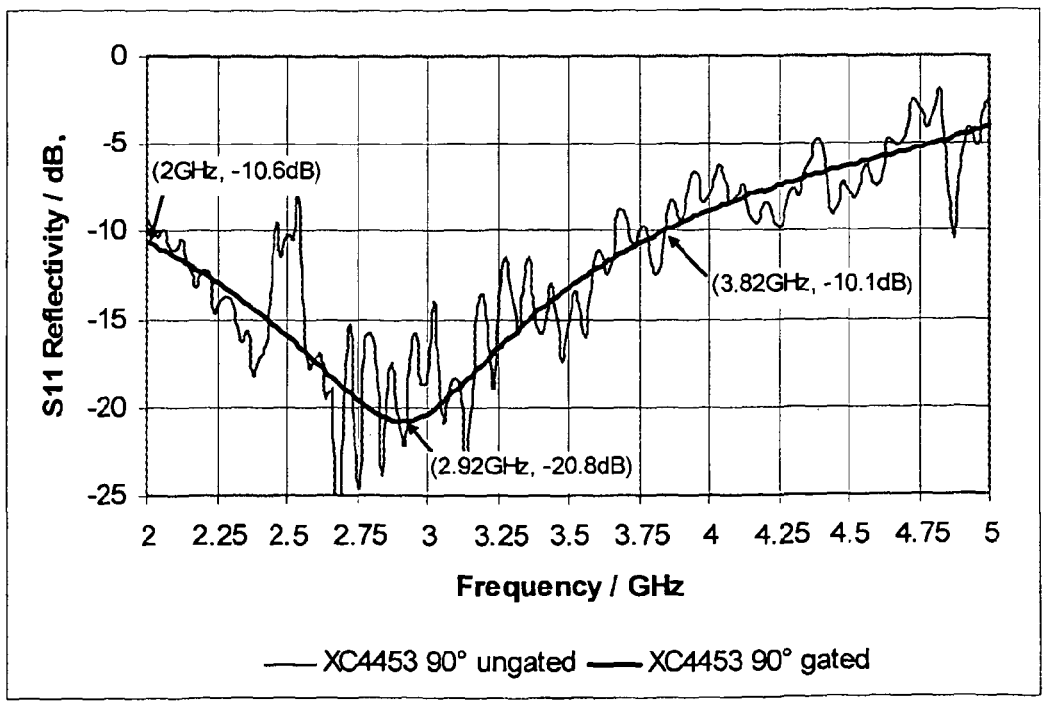
FIG. 4 shows graph of electromagnetic reflectivity versus frequency of electromagnetic radiation measured using an HP8722C Vector Network Analyser (VNA) for a sample article reference XC4453 at 90° sample orientation.

The set up and method has been validated against sample article XC4453, which varies with sample orientation. The response of the sample article is shown in FIGS. 3 and 4 for gated and un-gated data. As described above, a 2 ns span gate was used in the experimental measurements. It can be seen that the gating removes a significant amount of the noise in the results.

FIG. 3 illustrates the Reflectivity of sample XC4453 at 0° sample orientation (i.e. 0° sample direction parallel to E-field). Gate details: gate centre=0 s, gate span=2 ns FIG. 4 illustrates the Reflectivity of sample XC4453 at 90° sample orientation (i.e. 90° sample direction parallel to E-field). Gate details: gate centre=0 s, gate span=2 ns Reflectivity measurements were also conducted using the apparatus of FIG. 2 including an Anritsu VNA Master Vector Network Analyser (VNA).

The set up and method was again validated against sample article XC4453, which varies with sample orientation. The Anritsu VNA Master VNA is a pre-production VNA and currently cannot be used to apply a gate on the instrument. The un-gated data is saved as real and imaginary S-parameters and therefore can be gated using a Mathcad program. The response of the sample article is shown in FIGS. 5 and 6 for un-gated data.

Figure 5:
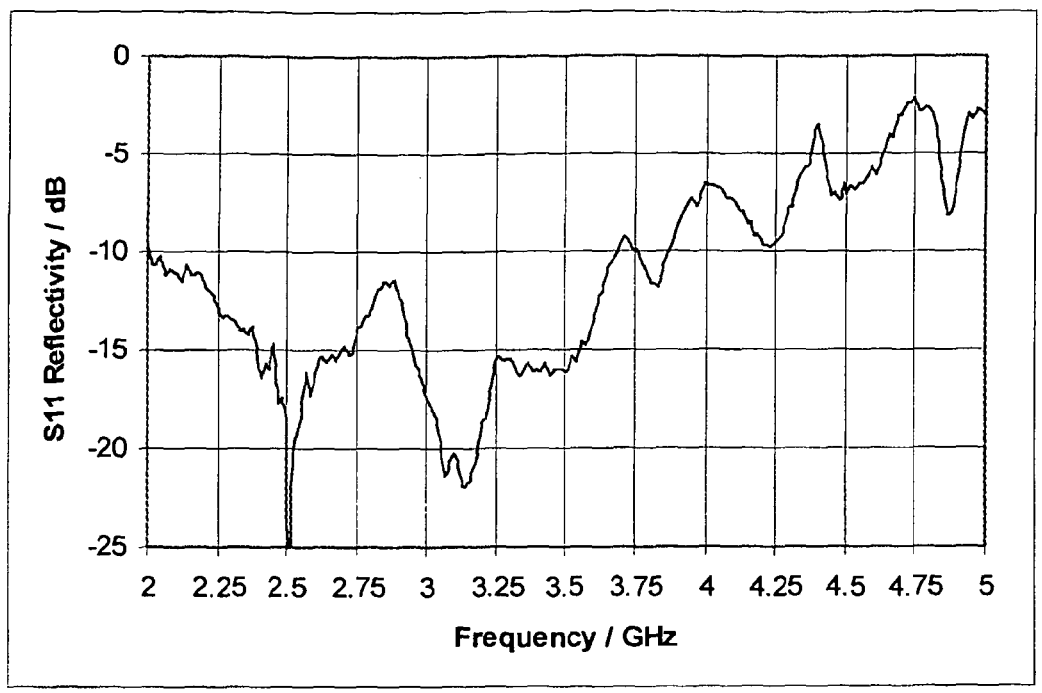
FIG. 5 shows a further graph of electromagnetic reflectivity versus frequency of electromagnetic radiation measured using an Anritsu VNA Master Vector Network Analyser (VNA) for a sample article reference XC4453 at 0° sample orientation.

FIG. 5 illustrates the Reflectivity of sample XC4453 at 0° sample orientation

Figure 6:
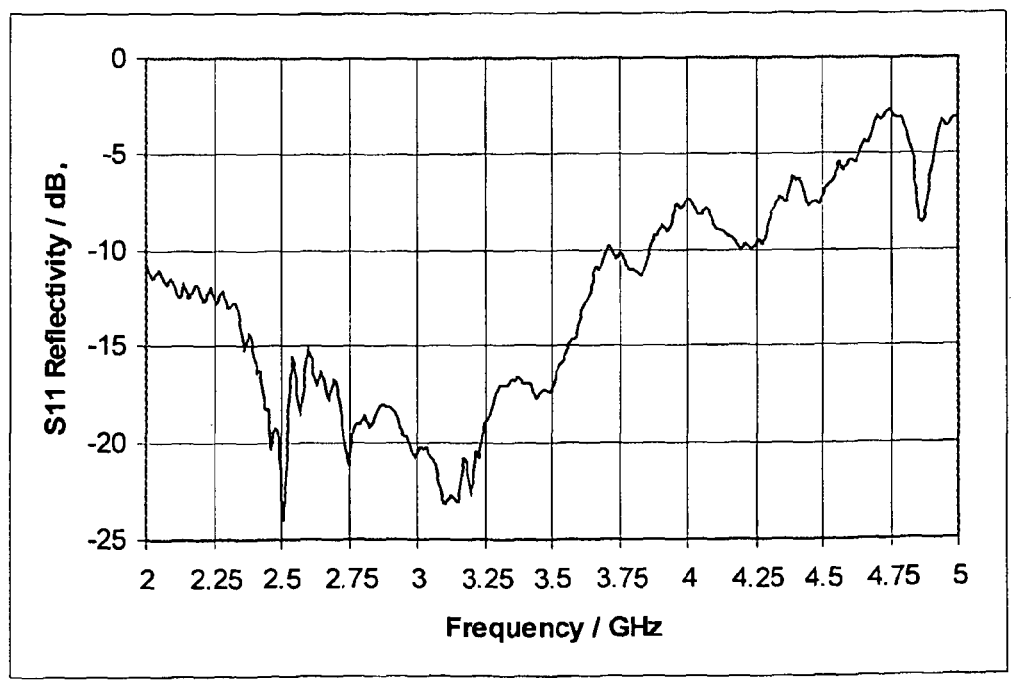
FIG. 6 shows a further graph of electromagnetic reflectivity versus frequency of electromagnetic radiation measured using an Anritsu VNA Master Vector Network Analyser (VNA) for a sample article reference XC4453 at 90° sample orientation.

FIG. 6 illustrates the Reflectivity of sample XC4453 at 90° sample orientation

The method and reflectometer is used primarily for reflectivity measurements, but can be converted to other data such as permittivity. The method and reflectometer apparatus has been demonstrated for frequencies ranging from 1 to 18 GHz, but the technique is valid outside this range, dependent upon the limitations of the horn antenna 4.

In view of the foregoing description it will be evident to a person skilled in the art that various modifications may be made within the scope of the invention.

Each feature disclosed in the description, and (where appropriate) the claims and drawings may be provided independently or in any appropriate combination.

In particular, with reference to the appended claims, features from dependent claims may be combined with those of the independent claims and features from respective independent claims may be combined in any appropriate manner and not merely in the specific combinations enumerated in the claims.

The invention claimed is:

1. A method of measuring the reflectivity of a region of an article to electromagnetic radiation comprising the steps of:
   a) arranging the article in the near-field of a transceiver antenna,
   b) aligning the antenna along a direction substantially orthogonal to a surface of the region to be measured and at a predetermined distance from said surface,
   c) illuminating the region of the article with electromagnetic radiation transmitted from the antenna over a desired frequency range,
   d) receiving electromagnetic radiation reflected from the region of the article in the near-field of the antenna using said antenna,
   e) measuring the reflected radiation and determining therefrom the reflectivity of said article in said region;
   wherein at least one substantially rigid spacing member is provided in mechanical communication with the article and the antenna so as to align the antenna, and
   the spacing member comprises an optical element comprising a polymer foam disposed between the antenna and the article and wherein the illuminating and measuring steps are performed through said optical element.

2. A method according to claim 1 wherein the measuring step comprises measuring at least one of the magnitude and phase of the electromagnetic radiation reflected from said region of said article.

3. A method according to claim 2 wherein the measuring step comprises at least one of an S11 and an S22 reflectivity measurement.

4. A method according to claim 1 comprising determining the reflectivity using only reflected electromagnetic radiation received at the antenna within a predefined temporal window following the transmission of said electromagnetic radiation.

5. A method according to claim 1 wherein the illuminating step comprises illuminating the region with electromagnetic radiation having one of single and dual polarisation in a beam having a Gaussian intensity profile, and wherein the measuring step comprises measuring the reflected electromagnetic radiation at the or each polarisation state.

6. A method according to claim 1 wherein the electromagnetic radiation has a frequency in the range 1-20 GHz, particularly in the range 1-5 GHz, in particular about 3 GHz.

7. A method according to claim 1 comprising the step of determining at least one of the electromagnetic absorbency, a dielectric property and the relative permittivity of said article in said region from the determined electromagnetic reflectivity.

8. A method according to claim 1 comprising the step of measuring the reflectivity of a plurality of regions of said article to electromagnetic radiation.

9. A method according to claim 1 further including a calibration step comprising:
   f) measuring the electromagnetic reflectivity of a substantially reflective material and calibrating the determining step to provide a determined reflectivity of 0 (±1)dB, and
   g) measuring the electromagnetic reflectivity of a substantially absorptive material and calibrating the determining step to provide a determined reflectivity loss of >25 dB.

10. A method according to claim 1 wherein the spacing member comprises a plurality of legs depending from the antenna.

11. A method according to claim 1 wherein the polymer foam has a permittivity substantially the same as air.

12. A method according to claim 1 wherein the polymer foam comprises at least one of a synthetic polymer foam, a closed cell polymer foam, a microcellular polymer foam, a polythene foam and expanded polystyrene.

13. A method of measuring the electromagnetic reflectivity of an aerofoil structure, in particular a wind-turbine blade, using a method according to claim 1.

14. A reflectometer comprising a transceiver antenna having a spacing member depending there-from, the spacer member defining a measurement region within the near-field of the antenna within which to admit articles to measured, wherein the spacing member comprises an optical element arranged in optical and mechanical communication with the antenna, the optical element having a substantially planar surface within the measurement region, said planar surface being arranged substantially orthogonal to a transceiving axis of the antenna.

15. A reflectometer according to claim 14 wherein the spacing member comprises a plurality of legs depending from the antenna.

16. A reflectometer according to claim 14 wherein the optical element comprises a polymer foam having a permittivity substantially the same as air.

17. A reflectometer according to claim 14 wherein the measurement region is arranged in the range 50-500 mm from the antenna, in particular 100-300 mm meters from the antenna.

18. A reflectometer according to claim 16 wherein the polymer foam comprises at least one of a synthetic polymer foam, a closed cell polymer foam, a microcellular polymer foam, a polythene foam, and expanded polystyrene.

19. A reflectometer according to claim 14 wherein the antenna comprises a microwave horn antenna.

20. A reflectometer according to claim 14 adapted in use to emit a beam of microwave radiation having a substantially Gaussian intensity profile and one of single and dual polarisation.

21. A reflectometer according to claim 14 including a source of electromagnetic radiation having a frequency in the range 1-20 GHz, particularly in the range 1-5 GHz, in particular about 3 GHz.

22. A reflectometer according to claim 14 wherein the source and receiver are configured in use to perform one of an S11 and an S12 reflectivity measurement.

23. Use of an apparatus according to claim 14 to measure the electromagnetic reflectivity of an aerofoil structure, in particular a wind-turbine blade.

* * * * *